(12) United States Patent
Toguchi et al.

(10) Patent No.: US 10,429,339 B2
(45) Date of Patent: Oct. 1, 2019

(54) GAS SENSOR

(71) Applicant: DENSO CORPORATION, Kariya, Aichi-pref. (JP)

(72) Inventors: Kengo Toguchi, Kariya (JP); Masatake Nakamura, Kariya (JP)

(73) Assignee: DENSO CORPORATION, Kariya (JP)

( * ) Notice: Subject to any disclaimer, the term of this patent is extended or adjusted under 35 U.S.C. 154(b) by 304 days.

(21) Appl. No.: 15/326,726

(22) PCT Filed: Jul. 9, 2015

(86) PCT No.: PCT/JP2015/069713
§ 371 (c)(1),
(2) Date: Jan. 17, 2017

(87) PCT Pub. No.: WO2016/009929
PCT Pub. Date: Jan. 21, 2016

(65) Prior Publication Data
US 2017/0212072 A1      Jul. 27, 2017

(30) Foreign Application Priority Data
Jul. 17, 2014   (JP) .................................. 2014-147131

(51) Int. Cl.
*G01N 27/407*       (2006.01)
*G01N 27/409*       (2006.01)
(Continued)

(52) U.S. Cl.
CPC ........ *G01N 27/409* (2013.01); *G01N 27/4067* (2013.01); *G01N 27/4077* (2013.01); *G01N 33/0036* (2013.01)

(58) Field of Classification Search
CPC ............. G01N 27/407; G01N 27/4071; G01N 27/4077
See application file for complete search history.

(56) References Cited

U.S. PATENT DOCUMENTS 6,348,141 B1 *   2/2002   Kato .................. G01N 27/4077
                                                              204/426
7,390,385 B2 *   6/2008   Ikoma ................ G01N 27/4077
                                                              204/424
(Continued)

FOREIGN PATENT DOCUMENTS

DE      19924319 C2 *   5/2001   ............. G01N 27/12
JP      5-249069             9/1993

OTHER PUBLICATIONS

EPO computer-generated English language translation of the Description section of DE 19924319 C2 (published May 17, 2001). Downloaded Jan. 9, 2019. (Year: 2019).*

*Primary Examiner* — Alexander S Noguerola
(74) *Attorney, Agent, or Firm* — Nixon & Vanderhye, P.C.

(57) ABSTRACT

A gas sensor includes a solid electrolyte body provided with a measured gas side electrode and a reference gas side electrode, a heater in the solid electrolyte body, a housing for holding the solid electrolyte body therein, and a cover for covering the solid electrolyte body. The cover has a large-diameter cover portion positioned on an outer circumferential side of the solid electrolyte body, a small-diameter cover portion positioned adjacent to a tip side of the large-diameter cover portion and formed smaller than the large-diameter cover portion, and a stepped portion connecting the small-diameter cover portion and the large-diameter cover portion. A first through hole is formed at a tip of the small-diameter cover portion. A second through hole is formed at a plurality of positions in a circumferential direction of the stepped portion.

7 Claims, 4 Drawing Sheets

(51) Int. Cl.
*G01N 27/406* (2006.01)
*G01N 33/00* (2006.01)

(56) References Cited

U.S. PATENT DOCUMENTS

| | | | |
|---|---|---|---|
| 2007/0215468 A1* | 9/2007 | Hirose | G01N 27/4071 204/424 |
| 2008/0073209 A1 | 3/2008 | Yamada | 204/424 |
| 2008/0223110 A1 | 9/2008 | Weyl et al. | 73/31.05 |
| 2011/0094883 A1* | 4/2011 | Ito | G01N 27/4077 204/429 |
| 2013/0327121 A1 | 12/2013 | Shimazaki et al. | 73/23.2 |

\* cited by examiner

GAS SENSOR

This application is the U.S. national phase of International Application No. PCT/JP2015/069713 filed Jul. 9, 2015 which designated the U.S. and claims priority from earlier Japanese Patent Application No. 2014-147131 filed Jul. 17, 2014, the entire contents of each of which are hereby incorporated by reference.

TECHNICAL FIELD

The present invention relates to a gas sensor for measuring oxygen concentration and the like in a measured gas.

BACKGROUND ART

A gas sensor disposed in an exhaust pipe of an internal combustion engine and measures oxygen concentration and the like in an exhaust gas passing through the exhaust pipe is required to have responsiveness indicating the speed of measurement, water resistance indicating protection from moisture, and the like.

For example, Patent Document 1 discloses a gas sensor including a detection element, a main fitting for holding the detection element, and a protector for accommodating a detection part of the detection element. The protector has a large-diameter portion and a small-diameter portion. A first tip wall of the large-diameter portion is provided with a first depressed portion recessed toward a rear end side in an axial direction and a first opening portion opening in the first depressed portion. In addition, a second tip wall of the small-diameter portion is provided with a second depressed portion recessed toward the rear end side in the axial direction and a second opening portion opening in the second depressed portion. Then, even when water droplets infiltrate into the protector from the first opening portion or the second opening portion, water droplets adhere to the first depressed portion or the second depressed portion, thereby preventing the water droplets from adhering to the detecting element.

PRIOR ART

Patent Document

[Patent Document 1] Japanese Patent Application Laid-Open Publication No. 2013-257192

DISCLOSURE OF THE INVENTION

Problems to be Solved by the Invention

However, the first depressed portion and the second depressed portion protrude toward an inside of the protector so as to block a flow of a measured gas passing through the first opening or the second opening. Therefore, the time for the measured gas to reach the detection part of the detection element is delayed, and the response of measurement by the gas sensor cannot be sufficiently improved.

The present invention has been made in light of the problems set forth above and has as its object to provide a gas sensor that can secure water resistance and increase a responsiveness of measurement.

Means for Solving the Problems

A gas sensor according to a first aspect includes a cup-shaped solid electrolyte body having oxygen ion conductivity in which a tip of a tubular outer circumferential portion is closed, a measuring gas side electrode disposed on an outer circumferential surface of the outer circumferential portion, a reference gas side electrode disposed on an inner circumferential surface of the outer circumferential portion, a heater disposed on an inner circumferential side of the solid electrolyte body for heating the solid electrolyte body, a housing for holding the solid electrolyte body, and a cover attached to the housing for covering the solid electrolyte body. The cover has a large-diameter cover portion positioned on an outer circumferential side of the solid electrolyte body, a small-diameter cover portion positioned adjacent to a tip side of the large-diameter cover portion and formed smaller in diameter than the large-diameter cover portion, and a stepped portion connecting the small-diameter cover portion and the large-diameter cover portion. A first through hole having the entire circumference of a hole punched out is formed at a tip of the small-diameter cover portion, and a second through hole having the entire circumference of a hole punched out is formed at a plurality of positions in a circumferential direction of the stepped portion.

Effects of the Invention

The cover is formed in a two-step shape of the large-diameter cover portion and the small-diameter cover portion in the gas sensor. Then, the first through hole that has the entire circumference of the hole punched out is formed at the tip of the small-diameter cover portion, and the second through hole that has the entire circumference punched out is formed at the plurality of positions in the circumferential direction of the stepped portion that connects the large-diameter cover portion and the small-diameter cover portion.

With the configuration of the cover, the measured gas easily passes between an outer side and an inner side of the cover via the first through hole and the second through hole. That is, it is possible to increase a flow speed of the measured gas in the vicinity of the measured gas side electrode. Then, the measured gas readily reaches the measured gas side electrode of the solid electrolyte body, and is easily discharged to the outside of the cover from the measured gas side electrode. Therefore, responsiveness of measuring the concentration of a specified gas component such as oxygen concentration by the gas sensor can be enhanced.

In addition, since the responsiveness of the gas sensor is enhanced, it is possible to keep the output of the heater low, so that the temperature of the solid electrolyte body is lowered. Thereby, it becomes possible to make water stress, cracks or the like due to moisture less likely to occur on the solid electrolyte body, and it is possible to obtain water resistance of the gas sensor. Further, moisture hardly infiltrates into the cover, and water resistance of the gas sensor can be obtained by minimizing hole diameters of the first through hole and the second through hole as much as possible. Therefore, it is possible to obtain water resistance and increase the responsiveness of measurement according to the above-described gas sensor.

The first through hole may be formed having a hole diameter of $\varphi$ 0.9 to 3 mm and is formed at one position, and the second through hole may be formed having a hole diameter of $\varphi$ 0.9 to 1.5 mm in the gas sensor.

In this case, the first through hole and the second through hole can be suitably made small, the passing of the measured gas is facilitated, and moisture can be prevented from infiltrating into the cover.

When the hole diameter of the first through hole is less than φ 0.9 mm and the hole diameter of the second through hole is less than φ 0.9 mm, it becomes difficult to manage the mold for forming the holes. On the other hand, when the hole diameter of the first through hole exceeds φ 3 mm and the hole diameter of the second through hole exceeds φ 1.5 mm, the water resistance deteriorates.

Further, a gap D1 between an inner circumferential surface of the large-diameter cover portion and the measured gas side electrode is within a range of 1 to 2.5 mm, the inner diameter D2 of the small-diameter cover portion is within a range of φ 3.8 to 9.8 mm, and a distance D3 from a tip of the measured gas side electrode to an base end surface of the stepped portion may be in the range of 1 to 6 mm.

In this case, a high flow speed of the measured gas in the vicinity of the measured gas side electrode can be maintained within the cover, and the responsiveness of measurement of the gas sensor can be maintained high.

The inner circumferential surface of the large-diameter cover portion and the measured gas side electrode may interfere with each other when the gap D1 is less than 1 mm. On the other hand, the responsiveness of the gas sensor may deteriorate when the gap D1 exceeds 2.5 mm.

The responsiveness of the gas sensor may deteriorate when the inner diameter D2 is less than φ 3.8 mm. On the other hand, it becomes difficult to establish the two-step shape between the large-diameter cover portion and the small-diameter cover portion when the inner diameter D2 exceeds φ9.8 mm.

The tip of the solid electrolyte body and the base end surface of the stepped portion may interfere with each other when the distance D3 is less than 1 mm. On the other hand, the responsiveness of the gas sensor may deteriorate when the distance D3 exceeds 6 mm.

MODE FOR CARRYING OUT THE INVENTION

Hereinafter, an embodiment relating to a gas sensor will be described with reference to the drawings.

Figure 1:
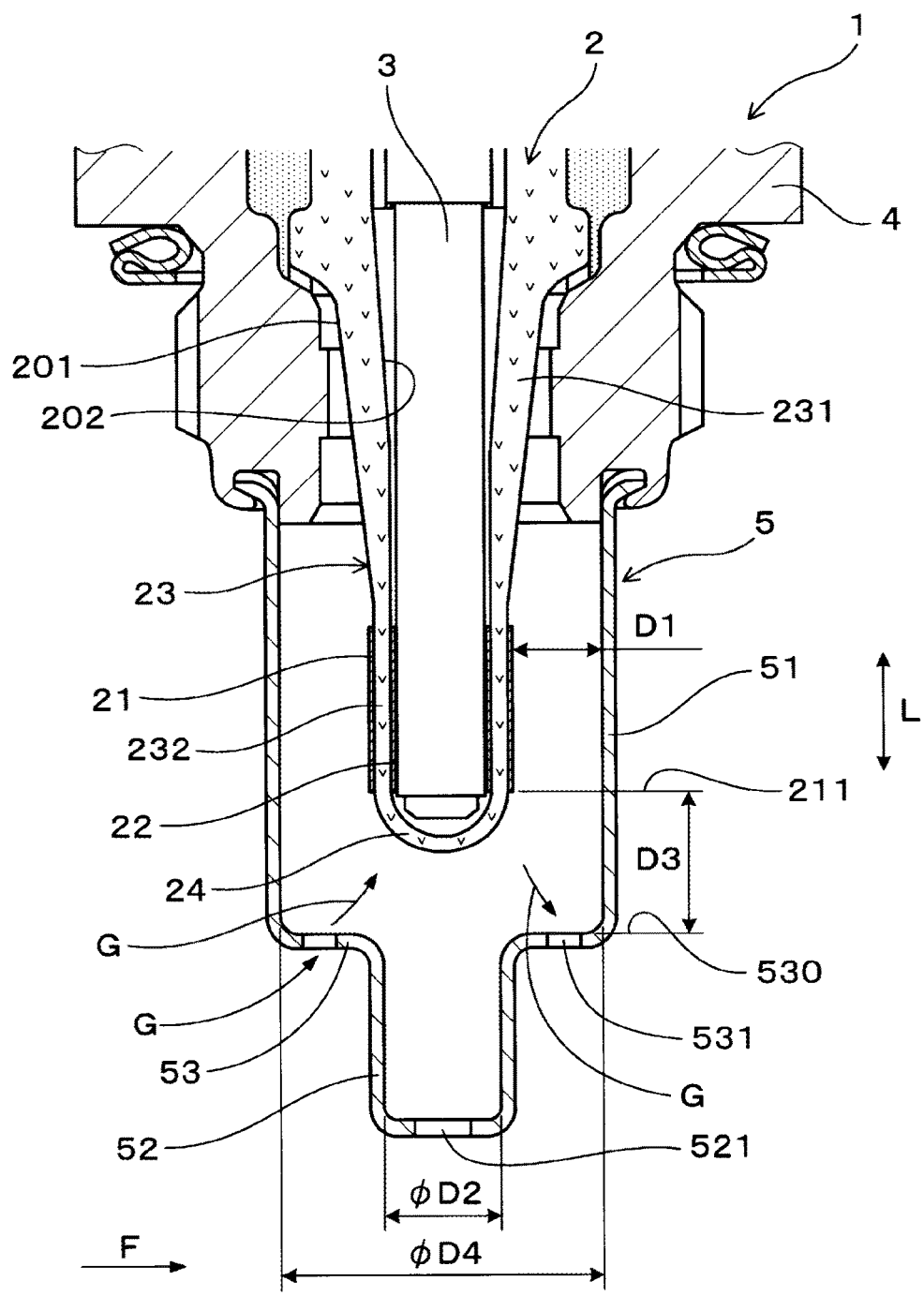
FIG. 1 is a sectional explanatory view showing a gas sensor according to an embodiment.

As shown in FIG. 1, the gas sensor 1 of the present embodiment includes a solid electrolyte body 2, a measured gas side electrode 21, a reference gas side electrode 22, a heater 3, a housing 4, and a cover 5. The solid electrolyte body 2 has oxygen ion conductivity and has a cup-shape in which a tip of a tubular outer circumferential portion 23 is closed. The measured gas side electrode 21 is disposed on an outer circumferential surface 201 of the outer circumferential portion 23 of the solid electrolyte body 2, and the reference gas side electrode 22 is disposed on an inner circumferential surface 202 of the outer circumferential portion 23. The heater 3 is disposed on an inner circumferential side of the solid electrolyte body 2, and is configured to heat the solid electrolyte body 2. The housing 4 has a tubular shape that holds the solid electrolyte body 2 in an inner circumferential side thereof. The cover 5 covers the solid electrolyte body 2, and a base end portion thereof is attached to the housing 4.

The cover 5 has a large-diameter cover portion 51 positioned on an outer circumferential side of the solid electrolyte body 2, a small-diameter cover portion 52 positioned adjacent to a tip side of the large-diameter cover portion 51 and formed smaller in diameter than the large-diameter cover portion 51, and a stepped portion 53 connecting the small-diameter cover portion 52 and the large-diameter cover portion 51. A first through hole 521 has the entire circumference of a hole punched out, that is, a perfect circle is formed at a tip of the small-diameter cover portion 52. A second through hole 531 has the entire circumference of a hole punched out, that is, a perfect circle is formed at a plurality of positions in a circumferential direction of the stepped portion 53.

Hereinafter, the gas sensor 1 of the present embodiment will be described in detail with reference to FIGS. 1 to 6.

As shown in FIG. 1, the gas sensor 1 of the present embodiment is used by being disposed in an exhaust pipe of a vehicle (not shown), and measures the oxygen concentration in an exhaust gas with the exhaust gas flowing through the exhaust pipe as a measured gas G. Further, the gas sensor 1 is disposed at a position on a downstream side of a position where a catalyst is disposed in the exhaust pipe, and is disposed substantially orthogonal to a flow F of the exhaust gas in the exhaust pipe.

In addition to the oxygen concentration sensor, the gas sensor 1 can be an A/F (air-fuel ratio) sensor or the like.

As shown in FIG. 1, the outer circumferential portion 23 of the solid electrolyte body 2 is formed in an inclined cylindrical shape in which an insertion portion 231 inserted through an inner circumferential hole of the housing 4 is reduced in diameter toward a tip end side, and a projecting portion 232 projecting toward the tip end side from the housing 4 is formed in a cylindrical shape parallel to an axial direction L of the gas sensor 1. A tip of the projecting portion 232 is closed by a hemispherical tip portion 24. The measured gas side electrode 21 is disposed on the entire circumference of the outer circumferential surface 201 of the projecting portion 232, and the reference gas side electrode 22 is disposed on the entire circumference of the inner circumferential surface 202 of the projecting portion 232. In addition, a gas sensor element is constituted by the solid electrolyte body 2, the measured gas side electrode 21, and the reference gas side electrode 22.

Although not shown in detail, the heater 3 is configured by disposing a conductor layer that generates heat by energization on a ceramic substrate. The conductor layer of the heater 3 is disposed in a range of the axial direction L in which the measured gas side electrode 21 and the reference gas side electrode 22 are disposed. The cover 5 has a structure in which the large-diameter cover portion 51, the stepped portion 53, and the small-diameter cover portion 52 are formed.

The large-diameter cover portion 51 and the small-diameter cover portion 52 of the cover 5 are formed in a cylindrical shape, and are disposed parallel to the axial direction L. The cover 5 is disposed coaxially with the solid electrolyte body 2. The projecting portion 232 of the solid electrolyte body 2 is disposed on the inner circumferential side of the large-diameter cover portion 51, and a predetermined gap D3 is formed between a tip 211 of the projecting portion 232 and a base end surface 530 of the stepped portion 53 of the cover 5.

The hole diameter of the first through hole 521 at the tip of the small-diameter cover portion 52 is within a range of φ 0.9 to 3 mm. The first through hole 521 is formed at one position of a center position of the tip of the small-diameter cover portion 52. The hole diameter of the second through hole 531 at the stepped portion 53 is within a range of φ0.9 to 1.5 mm. The second through holes 531 are formed at equal intervals in a plurality of positions in the circumferential direction around a central axis of the solid electrolyte body 2 and the cover 5.

Dimensional relationships between the cover 5, and the cover 5 and its surroundings are as follows.

As shown in FIG. 1, a radial gap D1 between the inner circumferential surface of the large-diameter cover portion 51 and the measured gas side electrode 21 is within a range of 1 to 2.5 mm. In addition, an inner diameter D2 of the small-diameter cover portion 52 is within a range of φ 3.8 to 9.8 mm. Further, a distance D3 in the axial direction L from the tip 211 of the measured gas side electrode 21 to the base end surface 530 of the stepped portion 53 is in a range of 1 to 6 mm.

Figure 2:
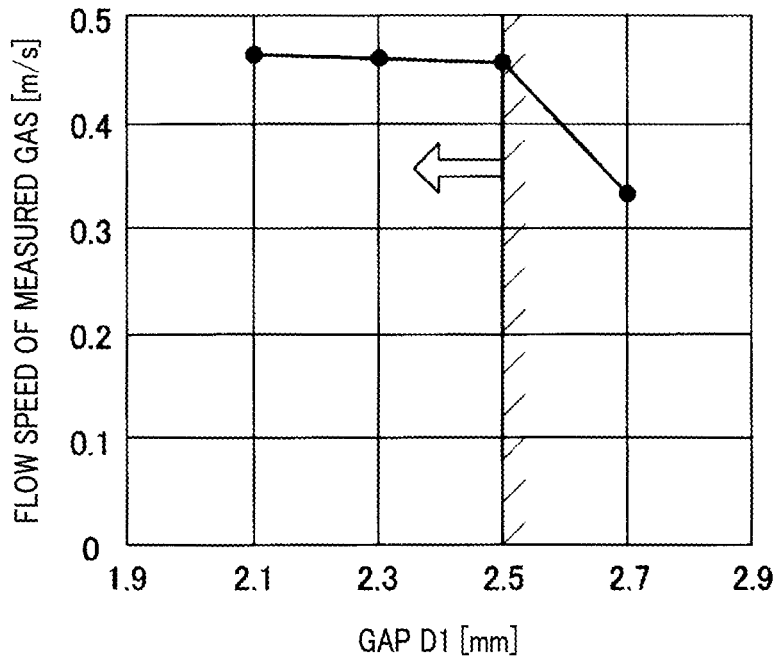
FIG. 2 is a graph showing a relationship between a gap D1 in a radial direction between an inner circumferential surface of a large-diameter cover portion and a measured gas side electrode on a horizontal axis and a flow speed of the measured gas in a vicinity of a measured gas side electrode of a solid electrolyte body on a vertical axis according to the embodiment.

FIG. 2 shows a relationship between the gap D1 (mm) and a flow speed (m/s) of the measured gas G in a vicinity of the measured gas side electrode 21 of the solid electrolyte body 2. In the graph, it is configured that the inner diameter D2 is φ 4 mm, the distance D3 is 3.5 mm, and the inner diameter D4 is φ 10 mm. As shown in the graph, when the gap D1 becomes larger than 2.5 mm, it is understood that the flow speed of the measured gas G decreases. The reason for this is considered to be that when the gap D1 is increased, a space into which the measured gas G flows becomes too wide between the large-diameter cover portion 51 and the projecting portion 232 of the solid electrolyte body 2. On the other hand, the flow speed of the measured gas G does not decrease and the responsiveness of measurement by the gas sensor 1 can be maintained high when the gap D1 is 2.5 mm or less. Further, it is preferable that the gap D1 is 1 mm or more in order to avoid interference between the inner circumferential surface of the large-diameter cover portion 51 and the measured gas side electrode 21.

Figure 3:
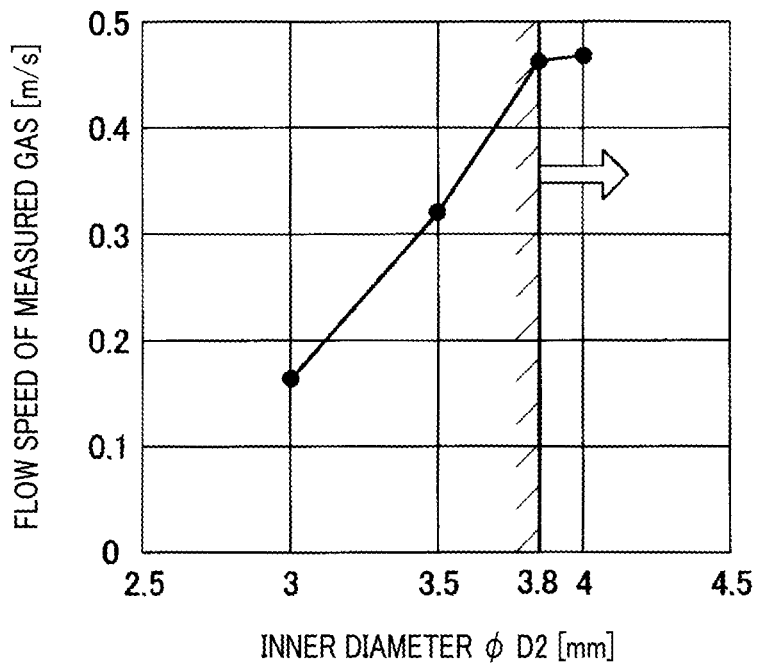
FIG. 3 is a graph showing a relationship between an inner diameter D2 of small diameter cover portion on a horizontal axis and the flow speed of the measured gas in the vicinity of the measured gas side electrode of the solid electrolyte body on the vertical axis according to the embodiment.

FIG. 3 shows a relationship between the inner diameter D2 (mm) and the flow speed (m/s) of the measured gas G in the vicinity of the measured gas side electrode 21 of the solid electrolyte body 2. In the graph, it is configured that the gap D1 is 2.3 mm, the distance D3 is 3.5 mm, and the inner diameter D4 is φ 10 mm. As shown in the graph, when the inner diameter D2 is smaller than φ 3.8 mm, it is understood that the flow speed of the measured gas G decreases. The reason for this is considered to be that when the inner diameter D2 becomes smaller, it is difficult for the measured gas G to flow through the small-diameter cover portion 52. On the other hand, the flow speed of the measured gas G does not decrease and the responsiveness of measurement by the gas sensor 1 can be maintained high when the inner diameter D2 is φ 3.8 mm or larger. Further, it is preferable that the inside diameter D2 is φ9.8 mm or less in order to establish the two-step shape between the large-diameter cover portion 51 and the small-diameter cover portion 52.

Figure 4:
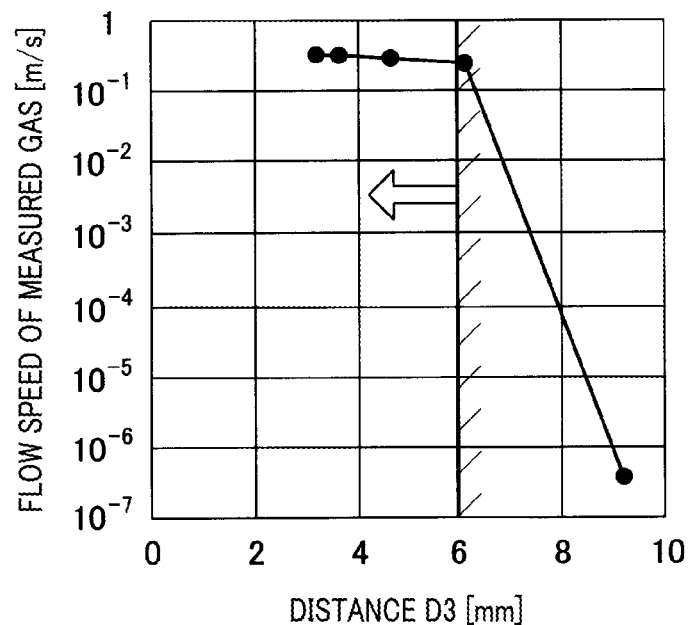
FIG. 4 is a graph showing a relationship between a distance D3 in an axial direction from a tip of the measured gas side electrode to a base end surface of a stepped portion on a horizontal axis and the flow speed of the measured gas in the vicinity of the measured gas side electrode of the solid electrolyte body on the vertical axis according to the embodiment.

FIG. 4 shows a relationship between the distance D3 (mm) and the flow speed (m/s) of the measured gas G in the vicinity of the measured gas side electrode 21 of the solid electrolyte body 2. In the graph, it is configured that the gap D1 is 2.3 mm, the inner diameter D2 is φ 4 mm, and the inner diameter D4 is φ 10 mm. As shown in the graph, it is understood that the flow speed of the measured gas G decreases when the distance D3 is larger than 6 mm. The reason for this is considered to be that the measured gas G hardly passes between the inside of the large-diameter cover portion 51 and the inside of the small-diameter cover portion 52 when the distance D3 is increased. On the other hand, the flow speed of the measured gas G does not decrease, and the responsiveness of measurement by the gas sensor 1 can be maintained high when the distance D3 is 6 mm or less. Further, the distance D3 is preferably 1 mm or more in order to avoid interference between the tip portion 24 of the solid electrolyte body 2 and the base end surface 530 of the stepped portion 53.

Further, as shown in FIG. 1, the inner diameter D4 of the large-diameter cover portion 51 is within the range of φ 8 to 14 mm. There is a possibility that the large-diameter cover portion 51 interferes with the measured gas side electrode 21 of the solid electrolyte body 2 when the inner diameter D4 of the large-diameter cover portion 51 is less than φ 8 mm. On the other hand, there is a possibility that the large-diameter cover portion 51 interferes with components around the large-diameter cover portion 51 when the inner diameter D4 of the large-diameter cover portion 51 exceeds φ 14 mm.

Further, opening areas of the entire second through holes 531 are in a range of 14 to 25 mm². The measured gas G hardly flows into the cover 5 when the total opening areas of the second through holes 531 become less than 14 mm², and the responsiveness of measurement by the gas sensor 1 may deteriorate. On the other hand, moisture easily permeates into the cover 5 from the second through holes 531 when the opening areas of the entire second through hole 531 exceed 25 mm², and the water resistance of the gas sensor 1 may deteriorate.

Figure 5:
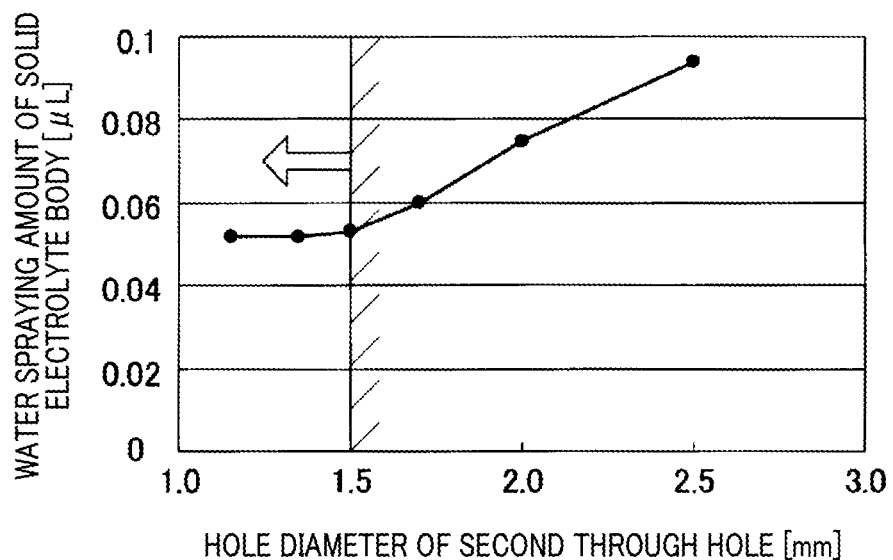
FIG. 5 is a graph showing a relationship between a hole diameter of a second through hole in the stepped portion of a cover on a horizontal axis and a water spraying amount of the solid electrolyte body on a vertical axis according to the embodiment.

FIG. 5 shows a relationship between the hole diameter (mm) of the second through hole 531 in the stepped portion 53 of the cover 5 and a water spraying amount (μL) of the solid electrolyte body 2. As shown in the graph, the water spraying amount of the solid electrolyte body 2 increases when the hole diameter of the second through hole 531 becomes larger than φ 1.5 mm. The reason for this is considered to be that that moisture scattered due to mixing with the measured gas G passes through the second through hole 531 and easily infiltrates into the cover 5 when the hole diameter of the second through hole 531 is increased. On the other hand, the solid electrolyte body 2 is less likely to be wetted, and the water resistance of the gas sensor 1 can be maintained high when the hole diameter of the second through hole 531 is φ 1.5 mm or less. Further, it is preferable that the hole diameter of the second through hole 531 is φ 0.9 mm or more in order to facilitate management of the mold for drilling the second through hole 531.

The cover 5 is formed in the two-step shape of the large-diameter cover portion 51 and the small-diameter cover portion 52 in the gas sensor 1 of the present embodiment. The first through hole 521 having the entire circumference of the small-diameter cover portion 52 punched out is formed, and the second through hole 531 having the entire circumference of the hole punched out is formed at the plurality of positions in the circumferential direction of the stepped portion 53 connecting the large-diameter cover portion 51 and the small-diameter cover portion 52.

With the configuration of the cover 5, the measured gas G easily passes between the outer side and the inner side of the cover 5 via the first through hole 521 and the second through holes 531. That is, with the configuration of the cover 5, the flow speed of the measured gas G in the vicinity of the measured gas side electrode 21 can be increased. Then, the measured gas G easily reaches the measured gas side electrode 21 of the solid electrolyte body 2, and is easily discharged from the measured gas side electrode 21 to the outside of the cover 5. Therefore, the responsiveness of measuring the oxygen concentration by the gas sensor 1 can be enhanced.

Figure 6:
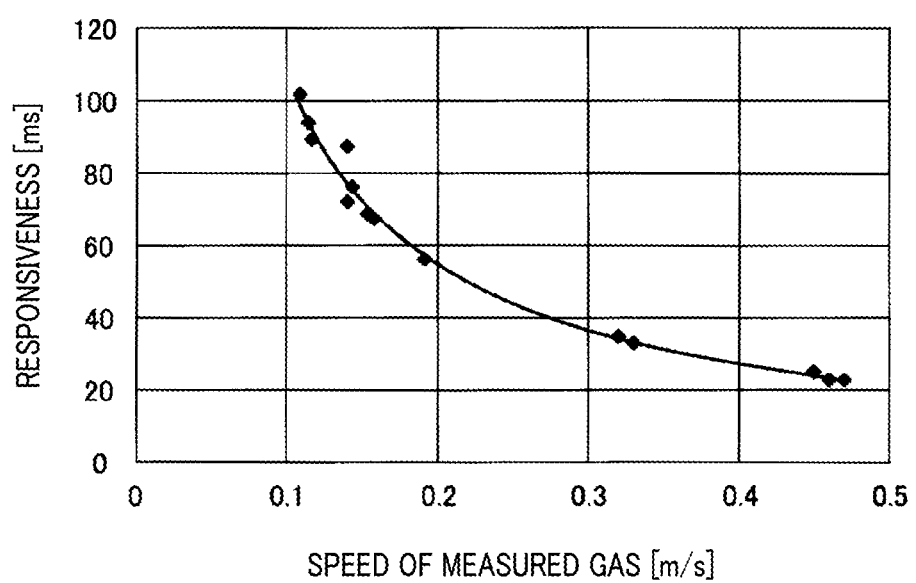
FIG. 6 is a graph showing a relationship between the flow speed of the measured gas in the vicinity of the measured gas side electrode of the solid electrolyte body on a horizontal axis and a response of the gas sensor on a vertical axis according to the embodiment.

FIG. 6 shows a relationship between the flow speed (m/s) of the measured gas G in the vicinity of the measured gas side electrode 21 of the solid electrolyte body 2 and the responsiveness (response time) (ms) of the gas sensor 1. As shown in the graph, as the flow speed of the measured gas G becomes faster, the responsiveness improves (response time becomes shorter). From this, it is understood that increasing the flow speed of the measured gas G in the vicinity of the measured gas side electrode 21 effectively contributes to enhancing the responsiveness of the gas sensor 1.

Further, by improving the responsiveness of the gas sensor 1, it is possible to keep the output of the heater 3 low, so that the temperature of the solid electrolyte body 2 (gas sensor element) is lowered. Thereby, it becomes possible to make water stress, cracks or the like due to moisture less likely to occur on the solid electrolyte body 2, and it is possible to obtain water resistance of the gas sensor 1. Further, moisture hardly infiltrates into the cover 5, and water resistance can be obtained by minimizing the hole diameter of the first through hole 521 to φ 3 mm or less and by minimizing the hole diameter of the second through hole 531 to φ 1.5 mm or less. Therefore, it is possible to obtain water resistance and increase the responsiveness of measurement according to the gas sensor 1 of the present embodiment.

REFERENCE SIGNS LIST

1: gas sensor
2: solid electrolyte body
201: outer circumferential surface
202: inner circumferential surface
21: measured gas side electrode
22: reference gas side electrode
23: outer circumferential portion
3: heater
4: housing
5: cover
51: large-diameter cover portion
52: small-diameter cover portion
521: first through hole
53: stepped portion
531: second through hole

The invention claimed is:

1. A gas sensor comprising:
a cup-shaped solid electrolyte body having oxygen ion conductivity in which a tip of a tubular outer circumferential portion is closed;
a measuring gas side electrode disposed on an outer circumferential surface of the outer circumferential portion;
a reference gas side electrode disposed on an inner circumferential surface of the outer circumferential portion;
a heater disposed on an inner circumferential side of the solid electrolyte body for heating the solid electrolyte body;
a housing for holding the solid electrolyte body; and
a cover attached to the housing for covering the solid electrolyte body; wherein,
the cover has a large-diameter cover portion positioned on an outer circumferential side of the solid electrolyte body, a small-diameter cover portion positioned adjacent to a tip side of the large-diameter cover portion and formed smaller in diameter than the large-diameter cover portion, and a stepped portion connecting the small-diameter cover portion and the large-diameter cover portion; wherein,
a first through hole having the entire circumference of a hole punched out is formed at a tip of the small-diameter cover portion; and
a second through hole having the entire circumference of a hole punched out is formed at a plurality of positions in a circumferential direction of the stepped portion,
wherein the cover is the only cover attached to the housing for covering the solid electrolyte body.

2. The gas sensor according to claim 1, wherein,
a hole diameter of the first through hole is within a range of φ0.9 to 3 mm; and
a hole diameter of the second through hole is in a range of φ0.9 to 1.5 mm.

3. The gas sensor according to claim 2, wherein,
the gas sensor is disposed at a position on a downstream side of a position where a catalyst is disposed in an exhaust pipe of a vehicle, and is disposed substantially orthogonal to a flow of an exhaust gas in the exhaust pipe.

4. The gas sensor according to claim 1, wherein,
the gas sensor is disposed at a position on a downstream side of a position where a catalyst is disposed in an exhaust pipe of a vehicle, and is disposed substantially orthogonal to a flow of an exhaust gas in the exhaust pipe.

5. A gas sensor comprising:
a cup-shaped solid electrolyte body having oxygen ion conductivity in which a tip of a tubular outer circumferential portion is closed;
a measuring gas side electrode disposed on an outer circumferential surface of the outer circumferential portion;
a reference gas side electrode disposed on an inner circumferential surface of the outer circumferential portion;

a heater disposed on an inner circumferential side of the solid electrolyte body for heating the solid electrolyte body;

a housing for holding the solid electrolyte body; and a cover attached to the housing for covering the solid electrolyte body; wherein, the cover has a large-diameter cover portion positioned on an outer circumferential side of the solid electrolyte body, a small-diameter cover portion positioned adjacent to a tip side of the large-diameter cover portion and formed smaller in diameter than the large-diameter cover portion, and a stepped portion connecting the small-diameter cover portion and the large-diameter cover portion; wherein, a first through hole having the entire circumference of a hole punched out is formed at a tip of the small-diameter cover portion; and a second through hole having the entire circumference of a hole punched out is formed at a plurality of positions in a circumferential direction of the stepped portion, wherein there are no intervening structures between the cup-shaped solid electrolyte body and interior surfaces of the cover except for the measuring gas side electrode and a portion of the housing.

6. The gas sensor according to claim 5, wherein, the gas sensor is disposed at a position on a downstream side of a position where a catalyst is disposed in an exhaust pipe of a vehicle, and is disposed substantially orthogonal to a flow of an exhaust gas in the exhaust pipe.

7. The gas sensor according to claim 5, wherein there are no intervening structures between the cup-shaped solid electrolyte body and interior surfaces of the large-diameter cover portion, the small diameter cover portion, and the stepped portion except for the measuring gas side electrode and a portion of the housing.

* * * * *